United States Patent [19]

Harle

[11] 4,391,138
[45] Jul. 5, 1983

[54] COLLECTING VESSEL

[76] Inventor: Anton Harle, Schelmenstiege 8, D-4400 Munster, Fed. Rep. of Germany

[21] Appl. No.: 272,990

[22] Filed: Jun. 12, 1981

[30] Foreign Application Priority Data

Jun. 21, 1980 [DE] Fed. Rep. of Germany ....... 3023348

[51] Int. Cl.³ .............................................. G01F 3/38
[52] U.S. Cl. ..................................... 73/223; 128/322
[58] Field of Search ......................... 73/219, 223, 427; 128/272, 760, 762, 766, 767, 771; 604/322, 326, 246

[56] References Cited

U.S. PATENT DOCUMENTS

| | | | |
|---|---|---|---|
| 3,888,236 | 6/1975 | Marx | 73/427 |
| 3,961,529 | 6/1976 | Hanifl | 73/219 |
| 4,000,649 | 1/1977 | Hanifl | 73/219 |
| 4,095,589 | 6/1978 | Manschot | 128/762 |
| 4,178,934 | 12/1979 | Forman | 128/762 |
| 4,305,404 | 12/1981 | Donn | 73/219 |

FOREIGN PATENT DOCUMENTS 2438154 8/1974 Fed. Rep. of Germany .
1477507 8/1974 United Kingdom .

Primary Examiner—S. Clement Swisher
Attorney, Agent, or Firm—Merchant, Gould, Smith, Edell, Welter & Schmidt

[57] ABSTRACT

The invention relates to a collecting vessel for medical purposes, i.e. medical fluids, which, in one-piece construction, forms a fluid collecting and measuring system and two pouch parts that can be joined together and with which inflow of the fluid, e.g. urine, can simultaneously be checked from the outside.

5 Claims, 5 Drawing Figures

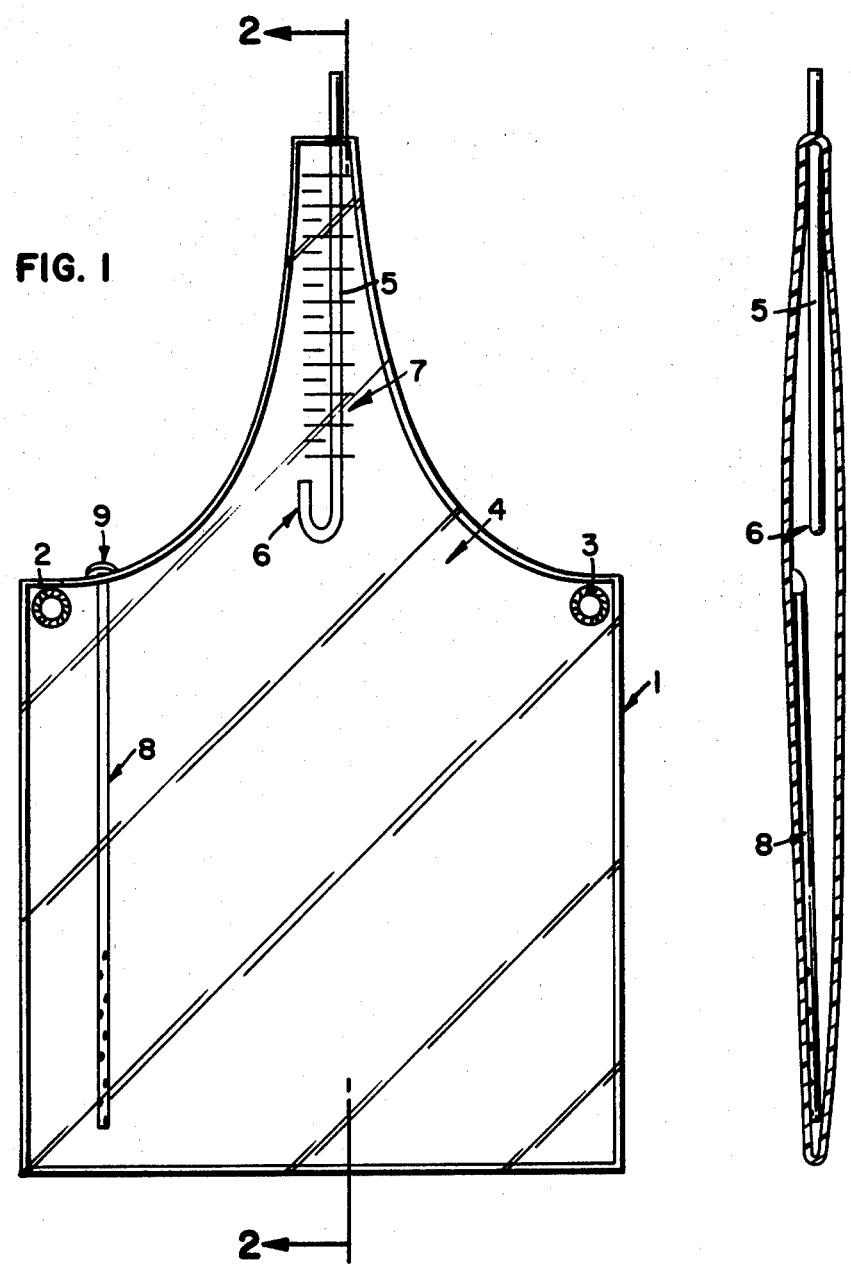

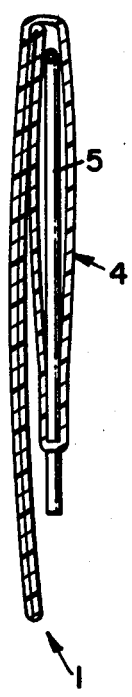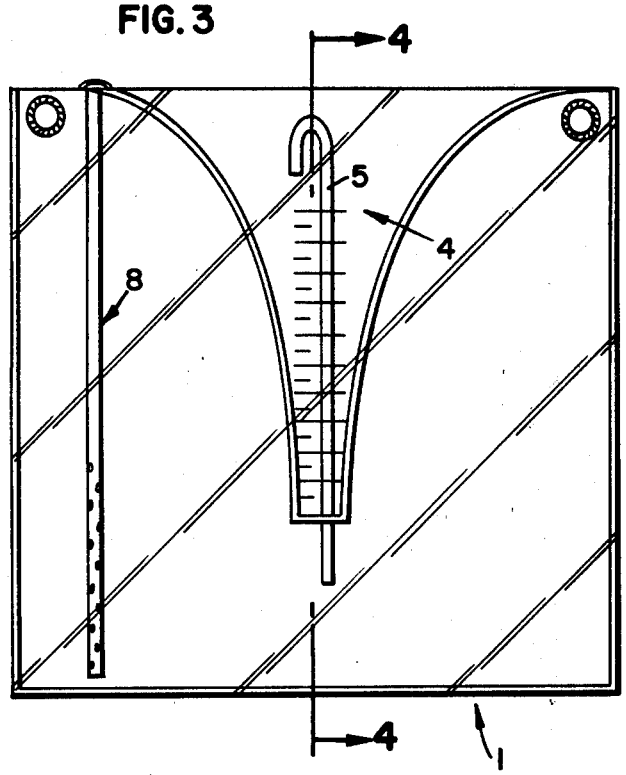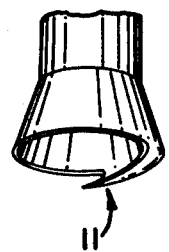

COLLECTING VESSEL

TECHNICAL FIELD

The invention relates to a collecting vessel for medical purposes, for example, for the collection of body fluids such as urine.

BACKGROUND OF THE INVENTION

In the case of the known urine collection equipment, emptying of the collection pouch was only possible by severing the connection between the catheter tube and the pouch. During this procedure, the exposed end of the catheter and the inside of the pouch were freely accessible to bacteria and the like. Another problem common to the known collection pouches was a determination of the quantity of urine flow. Typically, these known devices require the use of a urinometer with which it was possible to determine the flow of urine as a function of time. Also, in the case of these known devices, it was not possible to determine at first glance whether urine was flowing or not. Further, it was not possible to determine quickly how great the quantity of flowing urine was since the urine from the inflow tube moved down on the wall of the urine pouch. Connecting a urinometer into the fluid path was time consuming and tedious, and in turn, meant severance of the possibly sterile path between catheter and urine collection pouch.

The space requirement of the known systems was considerable since the urinometer tupically has a height of approximately 30 centimeters and requires a special suspending mechanism that makes the entire arrangement bulky and costly. Decontamination of such a large device is expensive.

Besides these purely technical disadvantages, the known systems additionally have the disadvantage that nursing personnel, and also the patient, can become infected with germs. Experience in the case of patient infection shows that, with the known drainage systems, about eighty percent of all patients become infected after two days on the system. This infection makes additional treatments necessary. It would naturally be advantageous to avoid these treatments.

Described in German Offenlegungsschrift No. 24 38 153, published Feb. 20, 1975, is an arrangement that consists of a rigid headpiece and an adjoining, firmly attached, flexible pouch part. Here, the rigid headpiece consists of a rigid device, preferably made of a duroplastic, equipped with a suspension means. A chamber constituting the measuring part is formed in this headpiece. Joined to the chamber is a connecting line to the pouch part. This connecting line must be manually manipulated for connection. Moreover, joined to the flexible pouch part is an emptying contrivance, and provided in the headpiece itself is an air opening equipped with a filter. This filter is in communication with the inside of the flexible pouch part through a second connecting line. This known device is extraordinarily bulky and does not represent a urine collection and measurement system which is closed to bacteria and germs.

SUMMARY OF THE INVENTION

The task set forth for the present invention is to obtain a closed fluid collecting and measuring system with which a rapid, trouble-free check of the actual flow of fluid is possible. Storage of the fluid, in a fashion safe against infection is desired. The pouch can be produced in such a cost-faborable and economical fashion that it can be constructed as a throw-away pouch.

The collecting vessel includes a throw-away, two-part pouch, having a conically tapered measuring pouch part and a main pouch part. The wide end of the tapered part is in fluid communication with the main part and a graduated measurement scale is positioned along the tapered part. An inflow tube passes through the measuring part and has a semicircular U-shaped bend at the end thereof. A pair of eyelets are located in the main part of the pouch so that when suspended the vessel folds over, its two pouch parts hanging from the eyelets.

In other words, through means of this design, a collecting vessel that can be produced with the same expenditure relative to manufacture as the previously known device is obtained. The instant invention is a simply constructed pouch that has the advantage that a conically tapered pouch part is folded over about a line of bend that lies approximately in the plane of the suspending means so that two pouch parts are obtained. The first part is a measuring part formed by the tapering pouch part. The second part is a collecting pouch which stores the greater quantities of fluid. The collecting pouch is formed by the pouch part adjoining the tapering pouch part.

In contrast to the known arrangements, overflow from one pouch part to the other part occurs automatically. Further, by simply raising the folded pouch part, the measuring pouch can be emptied into the main pouch part. In this way, urine is poured into the main pouch and a check of the newly inflowing urine is immediately possible.

If the inflow tube is equipped with a drip nose located at the end of the tube, inflow of the fluid into the pouch part does not occur at the rim of the pouch. With a drip nose, the urine drips down from the inflow tube so that the form and quantity of urine flow being discharged by the patient is easily seen.

Without contacting the fluid, a simple emptying of the tapering pouch into the main pouch part is possible. In this way it becomes possible at any time to remeasure inflowing fluid. Further, the main pouch part is also capable of being equipped with a graduated scale so that the total quantity of urine discharge can be measured there as well. Emptying of the pouch can actually be accomplished in a manner known per se by detaching the pouch from the catheter. However, it is also possible in accordance with a special feature of the invention, to undertake emptying of the pouch through a prick-through cap. The prick-through cap is positioned on the end of an emptying tube whereby it is absolutely impossible for the nurse to contact the patient's fluid, therefore, the transmittal of germs from the patient to the nurse is to a great extent excluded. The collecting vessel in accordance with the invention, can be mass produced from plastic foil in an economical fashion in the same manner as the known collecting pouches. This resolves the multiplicity of problems raised in the known pouches, and makes available to the practitioner an aid that essentially simplifies his daily work and that obtains for the nursing personnel improved working conditions. Obtained in particular is a closed system with which an interruption of the connection, as for the purposes of emptying the vessel or measuring the urine flow, is no longer required. Besides the capability of simple operation, decontamination is simplified and a urinometer is always supplied along with the pouch without incurring extra costs.

The preferred embodiment of the invention as a urine pouch will be described in the following description with the aid of the drawings.

FIG. 1 is an illustration of the urine pouch with the conical pouch part unfolded;

FIG. 2 is a cut along line 2—2 of FIG. 1;

FIG. 3 is the urine pouch in the in-use position with folded-down, conical pouch part;

FIG. 4 is a cut along line 4—4 in FIG. 3; and

FIG. 5 is a essentially larger scale, the arrangement of a drip-nose inside the tube end of the inflow tubing.

DETAILED DESCRIPTION OF THE INVENTION

Designated generally by 1 in the drawings is a urine pouch that is equipped with a suspending means consisting of eyelets 2 and 3. In the plane of the suspending means that is formed by the eyelets 2 and 3, adjoining the main pouch 1, there is a concially tapering, additional pouch part 4. Into the top part of pouch part 4 is incorporated an inflow tube 5 that is welded tightly with the upper edge of pouch part 4. The inflow tubing 5 is bent around semicircularly at its free end located inside the pouch, as is illustrated at 6. Additionally, the conically tapering pouch part displays a graduated measuring scale 7.

The conically tapering pouch part 4 is arranged offset somewhat so that, in the case of the illustration in accordance with FIG. 1, in the lefthand portion of the Figure, there is obtained a space for acceptance of a discharge tube 8. This discharge tube 8 is perforated at its lower end and terminates at the top end of the main pouch 1 with a prick-through cap 9. The prick-through cap 9 consists, as is known per se, of an elastic substance, preferentially gum rubber or synthetic rubber or the like. This substance displays a strength which, even in the case of manifold operation by means of a cannula, maintains good air tightness. Air tightness guarantees sealing of the penetrated region against the cannula as well as a tight closure of the working opening after withdrawal of the cannula.

Visible from the illustration in FIG. 3 is that, in the in-use position, the top conically tapering pouch part 4 can be folded about the line of bend lying in the region of the suspending means. In this position, conveying of the urine is accomplished through the connection part of the inflow tube 5. Hence, the urine drips out of the folded-over part 6 into the now downwardly conically tapering pouch part 4, and, here, the quantity of urine can be read off on the available measuring scale.

Additionally, the main pouch is equipped with a measuring scale that enables measurement of the urine given over from the auxiliary pouch part into the main pouch part.

It can be seen that, when using the pouch, there results, on the one hand, an automatic overflow of the urine out from the tapered pouch part 4 into the main pouch 1. However, emptying of the pouch part 4 into the main pouch part 1 is also possible at any time, so that the measurement of the inflowing urine can be done again at any time during the unit of time that is available.

FIG. 5 shows that the bent end 6 of the inflow tube 5 widens out conically and is equipped with a drip-nose 11, which ensures that no flow of urine occurs on the pouch wall, but rather that the urine drips freely from the tube opening into the tapered pouch part, so that it can be seen immediately from the outside whether or not urine is being discharged from the patient within a time control period.

Production of the pouch follows, in a manner known per se, from an appropriate plastic foil. The invention, however, is not limited to employment of this foil.

With this pouch formed in accordance with the invention, a single pouch is obtained that displays, at the lower end of pouch part 4, a precision measurement range. This fine measurement range is located in the top region of the pouch part 4, with a rough measurement region formed in the actual urine pouch 1. The pouch is closed on all sides and therewith makes possible a so-called "closed system". Emptying of the pouch is possible without the catheter connection between patient and pouch being interrupted so that infections are no longer possible. Aeration as in the previously known urinometers is no longer necessary.

While in the representation in accordance with FIGS. 3 and 4 the pouch part 4 lies immediately next to the wall of the main pouch 1, it is altogether possible to suspend the pouch, or to attach a cross piece in the region of the fold between the main pouch and the pouch part 4. With this arrangement, there arises an interval or space such that, when filling the pouch part 4, the pouch wall does not lie against the main pouch, so that influences upon the results of measurement from this are not possible.

I claim:

1. A flexible collecting vessel having a main pouch part and a measuring pouch part, said measuring part, being tapered and having a narrow end and a wide end, said wide end of said measuring part in fluid communication with said main part;
    a graduated measurment scale positioned along said tapered part, said graduations starting at said narrow end of said measuring part;
    an inflow tube having a free end, said tube passing through said narrow end of said measuring part and extending in a direction toward said main part for a distance and having a generally semicircular, U-shaped bend subtantially at said free end of said tube; and
    suspension means affixed to said main part between said measuring part and said main part, said suspension means for suspending said vessel in a folded-over fashion so that said narrow end of said measuring part hangs downwardly from said affixment of said suspension means.

2. The collecting vessel of claim 1 wherein said suspension means includes at least two eyelets lying in a plane, said eyelets forming a line of bend that lies approximately in the plane of the eyelets when said vessel is suspended.

3. The collecting vessel of claim 1 further comprising means for dripping fluid passing from said tube into said measuring pouch part.

4. The collecting vessel of claim 3 wherein said dripping means includes said tube free end having a conically widened portion.

5. The collecting vessel of claim 1 further comprising a discharge tube extending into said main pouch part, said discharge tube having a length, a first end sealed with a prick through cap located exterior of said vessel, a second end located interior of said vessel and perforations along said length near said second end.

\* \* \* \* \*

UNITED STATES PATENT AND TRADEMARK OFFICE
CERTIFICATE OF CORRECTION

PATENT NO. : 4,391,138
DATED : July 5, 1983
INVENTOR(S) : Dr. Anton Harle

It is certified that error appears in the above—identified patent and that said Letters Patent is hereby corrected as shown below:

Column 1, line 31, "tupically" should be --typically--;

Column 1, line 46, "153" should be --154--;

Column 2, line 29, "other part" should be --other pouch part--.

Signed and Sealed this

Eighteenth Day of October 1983

[SEAL]

Attest:

GERALD J. MOSSINGHOFF

Attesting Officer

Commissioner of Patents and Trademarks